United States Patent
Pinkovich et al.

(10) Patent No.: US 11,707,201 B2
(45) Date of Patent: Jul. 25, 2023

(54) METHODS AND SYSTEMS FOR MEDICAL IMAGING BASED ANALYSIS OF EJECTION FRACTION AND FETAL HEART FUNCTIONS

(71) Applicant: GE Precision Healthcare LLC, Milwaukee, WI (US)

(72) Inventors: Dani Pinkovich, Haifa (IL); Sarit Shwartz, Haifa (IL); Noa Alkobi, Haifa (IL); Robert Anderson, Oshkosh, WI (US); Antonio Fabian Fermoso, Madrid (ES); Walter Duda, Jr., Regau (AT); Christian Fritz Perrey, Mondsee (AT)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 581 days.

(21) Appl. No.: 16/811,628

(22) Filed: Mar. 6, 2020

(65) Prior Publication Data
US 2021/0275047 A1    Sep. 9, 2021

(51) Int. Cl.
| | |
|---|---|
| *A61B 5/024* | (2006.01) |
| *A61B 5/02* | (2006.01) |
| *A61B 5/055* | (2006.01) |
| *G06T 7/149* | (2017.01) |
| *G06T 7/246* | (2017.01) |
| *G06T 7/00* | (2017.01) |
| *A61B 5/344* | (2021.01) |

(52) U.S. Cl.
CPC ...... *A61B 5/02411* (2013.01); *A61B 5/02028* (2013.01); *A61B 5/055* (2013.01); *A61B 5/344* (2021.01); *G06T 7/0012* (2013.01); *G06T 7/149* (2017.01); *G06T 7/246* (2017.01); *G06T 2207/10081* (2013.01); *G06T 2207/10088* (2013.01); *G06T 2207/10132* (2013.01); *G06T 2207/20081* (2013.01); *G06T 2207/20084* (2013.01); *G06T 2207/30044* (2013.01); *G06T 2207/30048* (2013.01)

(58) Field of Classification Search
None
See application file for complete search history.

(56) References Cited

U.S. PATENT DOCUMENTS

| | | | |
|---|---|---|---|
| 2007/0135705 A1* | 6/2007 | Lorenz | G06T 7/20 600/410 |
| 2019/0125295 A1* | 5/2019 | Tek | A61B 8/469 |
| 2020/0160944 A1* | 5/2020 | Lynn | A61B 5/742 |
| 2021/0275047 A1* | 9/2021 | Pinkovich | G06T 7/12 |

OTHER PUBLICATIONS

Artificial intelligence to improve the diagnosis of cardiovascular diseases; Irene Fernández-Ruiz, PMID: 30683888; Mar. 2019 (Year: 2019).*

(Continued)

*Primary Examiner* — Nancy Bitar
(74) *Attorney, Agent, or Firm* — McAndrews, Held & Malloy, Ltd.; Jacob Groethe; David Bates

(57) ABSTRACT

Systems and methods are provided for enhanced heart medical imaging operations, particularly as by incorporating use of artificial intelligence (AI) based fetal heart functional analysis and/or real-time and automatic ejection fraction (EF) measurement and analysis.

22 Claims, 11 Drawing Sheets

(56) References Cited

OTHER PUBLICATIONS

Dynamic real-time 4D cardiac MDCT image display using GPU-accelerated volume rendering, ZHang et a, Apr. 2009 (Year: 2009).*
Real-Time Automatic Ejection Fraction and Foreshortening Detection Using Deep Learning, Smistad et al Feb. 2020 (Year: 2020).*

* cited by examiner

300

310

320

330

METHODS AND SYSTEMS FOR MEDICAL IMAGING BASED ANALYSIS OF EJECTION FRACTION AND FETAL HEART FUNCTIONS

FIELD

Aspects of the present disclosure relate to medical imaging. More specifically, certain embodiments relate to methods and systems for medical imaging based analysis of ejection fraction and fetal heart functions, particularly using artificial intelligence (AI) based analysis.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

In some instances, medical imaging systems may be used to conduct particular types of examination. For example, in some instances, medical imaging systems may be used in examining the heart and functions thereof. Use of medical imaging systems in conjunction with such examination, however, poses certain challenges, particularly with respect to assessing outcome of the examination. Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for medical imaging based analysis of ejection fraction and fetal heart functions, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
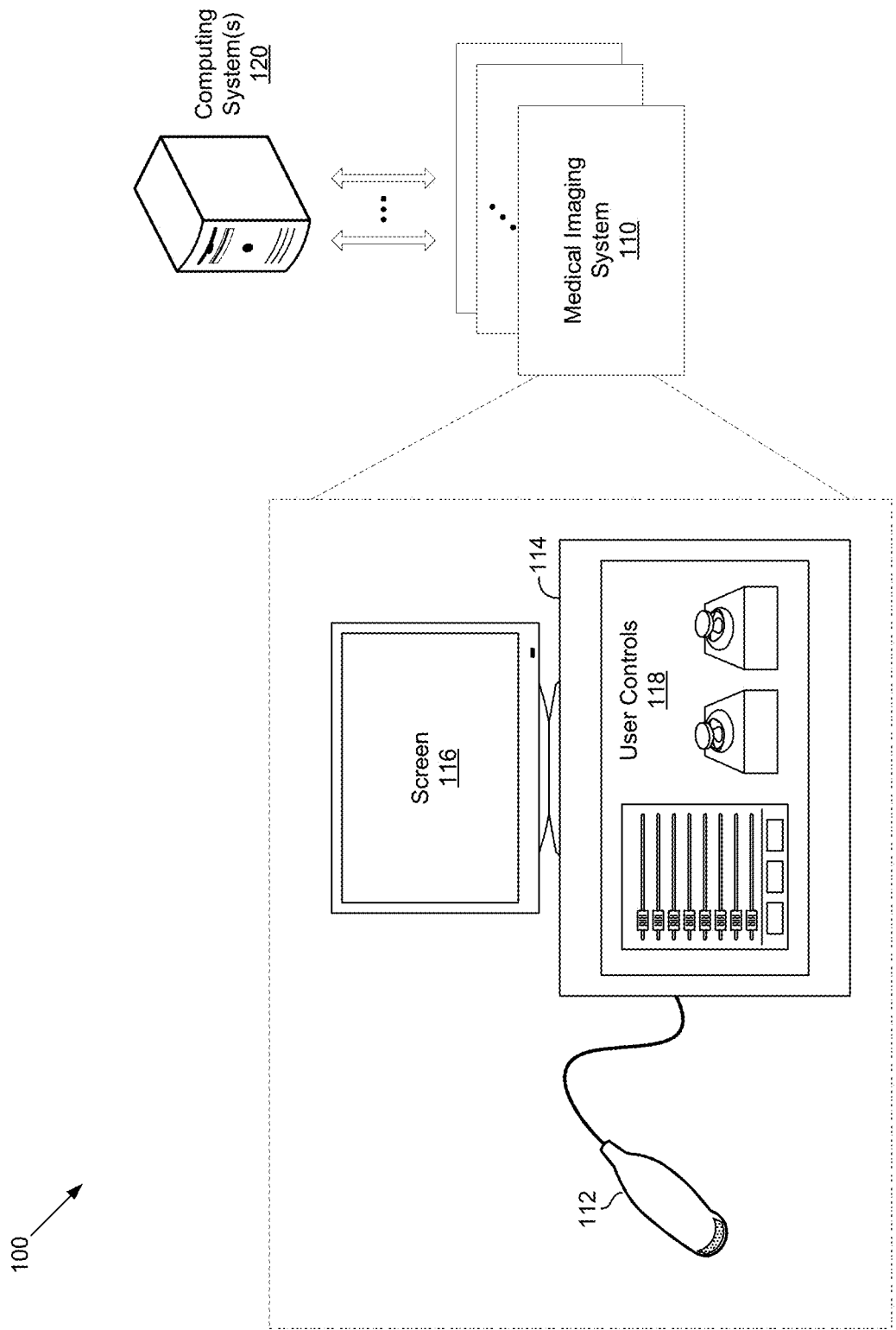
FIG. 1 is a block diagram illustrating an example medical imaging arrangement that may be configured for supporting medical imaging based analysis of ejection fraction and fetal heart functions.

Certain implementations in accordance with the present disclosure may be directed to medical imaging based analysis of ejection fraction and fetal heart functions. In particular, various embodiments have the technical effect of enhancing quality of heart examination using medical imaging, by allowing for automatic and real-time identification of one or more structures of the heart during the examination, particularly contour of a particular structure (e.g., a ventricle) in the heart, for visually identifying the contour in displayed images during the examination, and for measuring and/or calculation one or more parameters and/or indicators pertinent to the function of the heart during the examination. This may be done, for example, by use of artificial intelligence (AI) based techniques to facilitate the automatic identifying and/or calculation actions noted above. Aspects of the present disclosure have the technical effect of allowing for enhanced and more reliable heart examinations.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, processing to form images, including beamforming, is performed in software, firmware, hardware, or a combination thereof. One example implementation of an ultrasound system having a software beamformer architecture formed in accordance with various embodiments is illustrated FIG. 2.

FIG. 1 is a block diagram illustrating an example medical imaging arrangement that may be configured for supporting medical imaging based analysis of ejection fraction and fetal heart functions. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2. As shown in FIG. 1, the medical imaging system 110 may comprise a scanner device 112, which may be portable and movable, and a display/control unit 114.

The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost (by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other Cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, medical imaging systems (e.g., the medical imaging system 110) may be configured for supporting enhanced heart imaging operations, such as by incorporating use of artificial intelligence (AI) based fetal heart functional analysis and/or real-time and automatic ejection fraction (EF) measurement and analysis, as described in more detail below.

Figure 2:
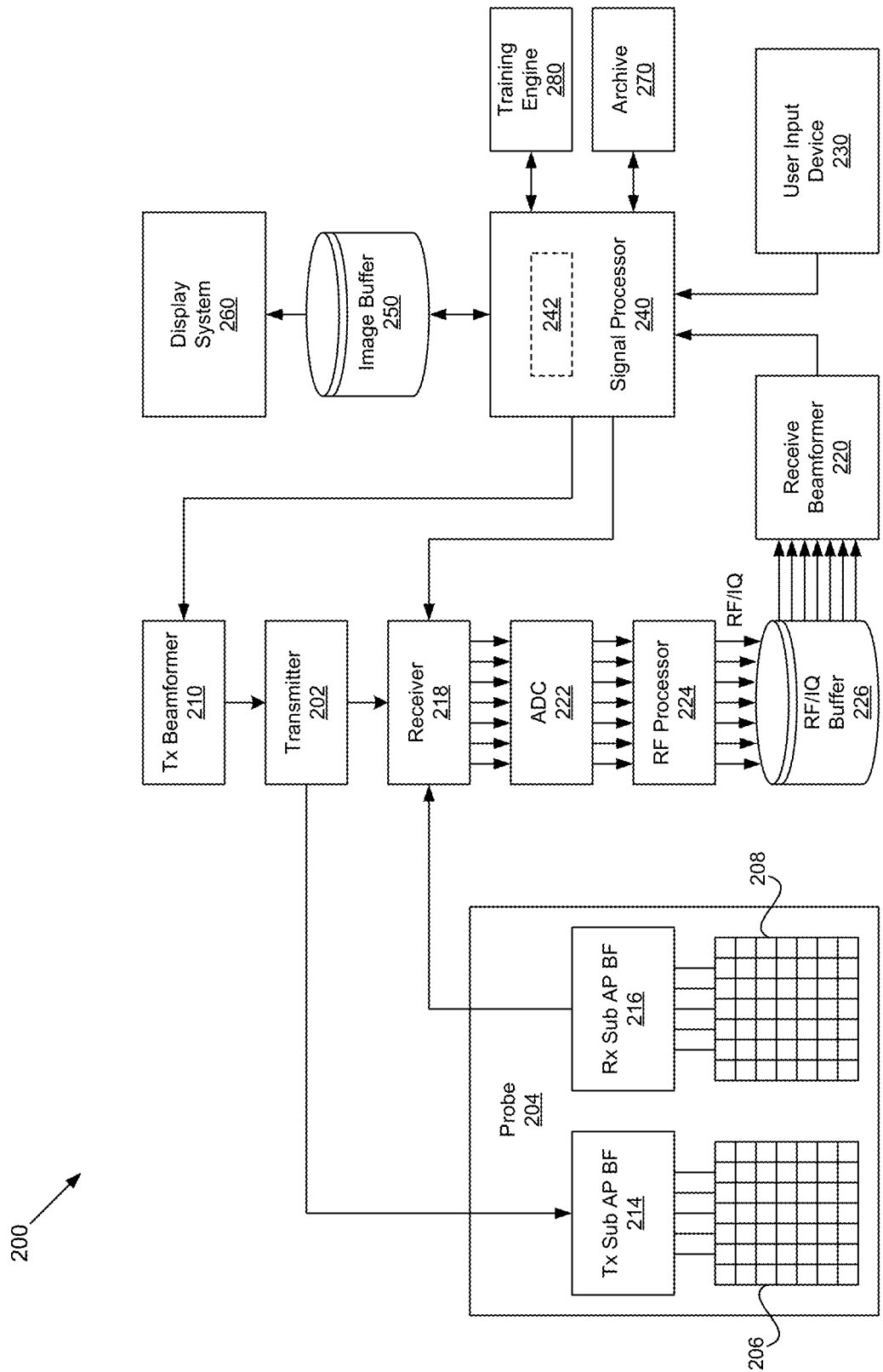
FIG. 2 is a block diagram illustrating an example ultrasound system that may be configured for supporting medical imaging based analysis of ejection fraction and fetal heart functions.

FIG. 2 is a block diagram illustrating an example ultrasound system that may be configured for supporting medical imaging based analysis of ejection fraction and fetal heart functions. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1.

The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example.

As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. In some instances, the user input device 230 may include, additionally and/or alternatively, image analysis processing to identify probe gestures by analyzing acquired image data.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a heart imaging module 242, which comprises suitable circuitry, interfaces, logic, and/or code that may be configured to perform and/or support various functions or operations relating to, or in support of enhanced medical imaging of the heart, particularly by use of artificial intelligence (AI) based fetal heart functional analysis and/or real-time and automatic ejection fraction (EF) measurement and analysis, as described in more detail below.

In some implementations, the signal processor 240 (and/or components thereof, such as the heart imaging module 242) may be configured to implement and/or use artificial intelligence and/or machine learning techniques to enhance and/or optimize imaging related functions or operations. For example, the signal processor 240 (and/or components thereof, such as the heart imaging module 242) may be configured to implement and/or use deep learning techniques and/or algorithms, such as by use of deep neural networks (e.g., a convolutional neural network (CNN)), and/or may utilize any suitable form of artificial intelligence image analysis techniques or machine learning processing functionality, which may be configured to analyze acquired ultrasound images, such as to identify, segment, label, and track structures (or tissues thereof) meeting particular criteria and/or having particular characteristics.

In an example implementation, the signal processor 240 (and/or components thereof, such as the heart imaging module 242) may be provided as a deep neural network, which may be made up of, for example, an input layer, an output layer, and one or more hidden layers in between the input and output layers. Each of the layers may be made up of a plurality of processing nodes that may be referred to as neurons. For example, the deep neural network may include an input layer having a neuron for each pixel or a group of pixels from a scan plane of an anatomical structure. The output layer may have a neuron corresponding to a plurality of pre-defined structures or types of structures. Each neuron of each layer may perform a processing function and pass the processed ultrasound image information to one of a plurality of neurons of a downstream layer for further processing.

As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. Thus, the processing performed by the deep neural network (e.g., a convolutional neural network (CNN)) may allow for identifying biological and/or artificial structures in ultrasound image data with a high degree of probability.

In some implementations, the signal processor 240 (and/or components thereof, such as the heart imaging module 242) may be configured to perform or otherwise control at least some of the functions performed thereby based on a user instruction via the user input device 230. As an example, a user may provide a voice command, probe gesture, button depression, or the like to issue a particular instruction, such as to control various aspects of heart imaging related operations, including artificial intelligence (AI) based analysis of fetal heart functions and/or real-time and automatic ejection fraction (EF) related measurements and/or analysis, and/or to provide or otherwise specify various parameters or settings relating thereto, as described in more detail below.

The training engine 280 may comprise suitable circuitry, interfaces, logic, and/or code that may be operable to train the neurons of the deep neural network(s) of the signal processor 240 (and/or components thereof, such as the heart imaging module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the heart imaging module 242) with respect to the characteristics of the particular structure(s), such as the appearance of structure edges, the appearance of structure shapes based on the edges, the positions of the shapes relative to landmarks in the ultrasound image data, and the like, and/or with respect to characteristics of particular tissues (e.g., softness thereof). In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, medical imaging systems (e.g., the ultrasound system 200) may be configured for supporting enhanced heart imaging operations, such as by incorporating use of artificial intelligence (AI) based fetal heart functional analysis and/or real-time and automatic ejection fraction (EF) measurement and analysis, as described in more detail below.

Figure 3A:
FIGS. 3A-3B illustrate an example workflow for fetal heart functional analysis, in accordance with the present disclosure.
Figure 3A:
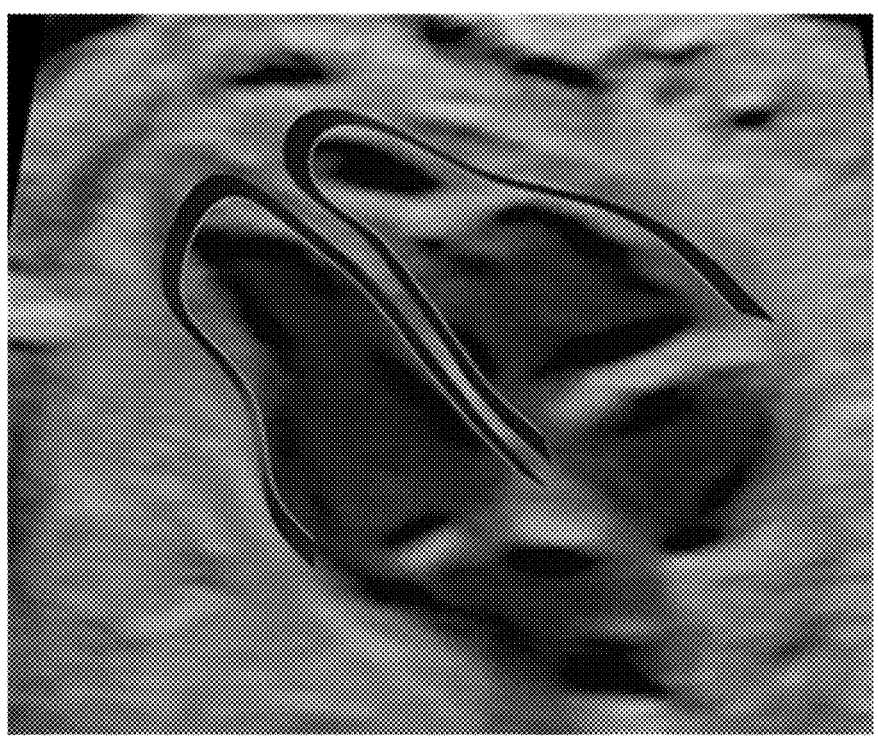
Figure 3B:
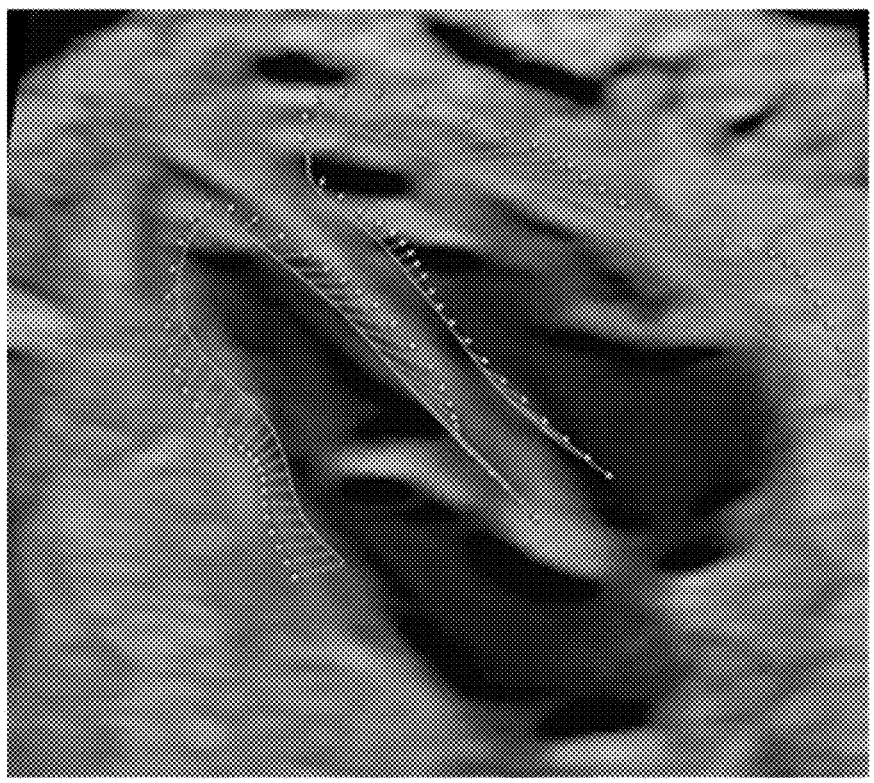
Figure 3B:

FIGS. 3A-3B illustrate an example workflow for fetal heart functional analysis, in accordance with the present disclosure. Shown in FIGS. 3A-3B is a sequence of screenshots generated in an example medical imaging system configured for supporting artificial intelligence (AI) based fetal heart functional analysis.

In various implementations, medical imaging systems (e.g., the ultrasound system 200 of FIG. 2) may be configured for artificial intelligence (AI) based fetal heart functional analysis. In this regard, functional analysis of the heart may entail acquiring a sequence of ultrasound images, automatically identifying, based on processing of the acquired images, particular structures in the heart (e.g., a particular ventricle, such as the left ventricle), then segmenting the endocardial or ventricle wall of heart (e.g., by identifying the contour of the ventricle, then selecting particular points on the contour), then tracking the wall motion over time (e.g., based on tracking of the contour point(s)) and computing functional parameters from the tracked contour point(s). In this regard, the automatic identifying of the particular structures in the heart may be performed using artificial intelligence and/or machine learning techniques, such as using deep learning techniques and/or algorithms (e.g., by use of deep neural networks, as described above). Typical functional parameters may include longitudinal or radial strain, strain rate, ejection fraction etc. Further, in some instances, speckle tracking techniques may be used for tracking the wall motion and visualize the tracked contour point(s) over one or more heart cycles.

Various issues may arise with convention approaches for conducting heart functional analysis, however. For example, identifying functional deficiencies of the fetal heart may be problems or even unfeasible. In this regard, in convention approaches, the heart motion pattern is assessed visually, and based on that assessment (or analysis) the user may determine whether (or not) the heart motion is normal. Clinical experts may be able to analyze the heart motion pattern visually, and often may be able to directly determine that the heart motion is not normal. Less experienced users may not be able to do so, however. Further, there may be cases where even expert users may miss something—e.g., subtle changes in heart dynamics and do not identify abnormal cases. The common approach to derive functional parameters from heart motion may also be problematic, because the motion information is reduced to only a few aspects (e.g., radial strain, diameter change from systole to diastole etc.).

Implementations in accordance with the present disclosure may address some of the issues associated with conventional approaches, particularly by reducing the problems and challenges mentioned above, such as by evaluating full set of information available (e.g., trajectory of contour points over the complete heart cycle) and by performing the analysis automatically, specifically using artificial intelligence (AI).

For example, in various implementations, an artificial intelligence (AI) framework may be used to perform at least some of the processing relating to the heart functional analysis. The AI framework may be implemented via suitable components in the medical imaging systems. For example, in the ultrasound system 200, the AI framework may be implemented via the signal processor 240, the heart imaging module 242, the training engine 270, etc. The trajectories of contour points of the fetal heart wall, for example, may be fed directly into the AI framework, which may be configured to discriminate normal and abnormal heart wall motion. Thus, an approach based on the present disclosure may reduce the complexity of functional heart analysis, such that it may be applied even by less experienced users. This may lead to reduced examination time, wider user acceptance, and/or reduction in the amount of missed fetal heart malformations.

In an example use scenario—e.g., corresponding to the screenshots illustrated in FIGS. 3A-3B—the user has to segment the inner wall of the left and right ventricle, as shown in screenshot 300. These contours may then be tracked over time, such as by tracking a set of contour points (e.g., using speckle tracking techniques). From the tracked contours in the systolic and diastolic phase several functional parameters may be calculated (e.g., changes in ventricle length and diameter between systole and diastole, area changes etc.). Comparing these parameters to previously derived statistics of normal hearts may give an indicator whether a heart behaves normal or not.

In addition to calculating functional parameters, the tracked contour point(s) may be visualized in several ways. For example, as illustrated in screenshot 310, the deformation may be shown in a color-coded way; screenshot 320 shows vectors that indicate the direction and magnitude of the wall deformation speed; whereas in screenshot 330 the trajectories of contour points are shown in a color-coded way—e.g., with the yellow dot indicating the position of a contour point at a current phase.

As noted above, currently applied methods may have some deficiencies. In this regard, reducing the functional information to several parameters implies that the available information is analyzed only partly (e.g., computation of radial strain or ejection fraction). Visualizing the dynamic information in motion videos (e.g., animated trajectories as shown in the screenshot 330) yields valuable information, but in a manner that may be useful only to experts. Thus, it is desirable to have a method for functional analysis of the fetal heart that takes advantage of the full set of available information and at the same time can be applied for non-experts. This may be achieved by utilizing processing resources in the medical imaging system implemented in accordance with the present disclose, particularly artificial intelligence related capabilities. For example, as described above, several contour points of the fetal wall are determined and tracked over time.

The contour trajectories may then be fed into the AI framework for classification. The AI framework may then be trained with contour trajectories from normal and diseases fetal hearts and will be trained to classify normal and abnormal heart motion. Such approach may take advantage of the full set of available information—e.g., the displacement trajectories as illustrated in screenshot 330, the direction and deformation speed as shown in screenshot 320, etc. Thus, instead of reducing the information to a few functional parameters, the deformation will be analyzed by an AI framework.

Figure 4:
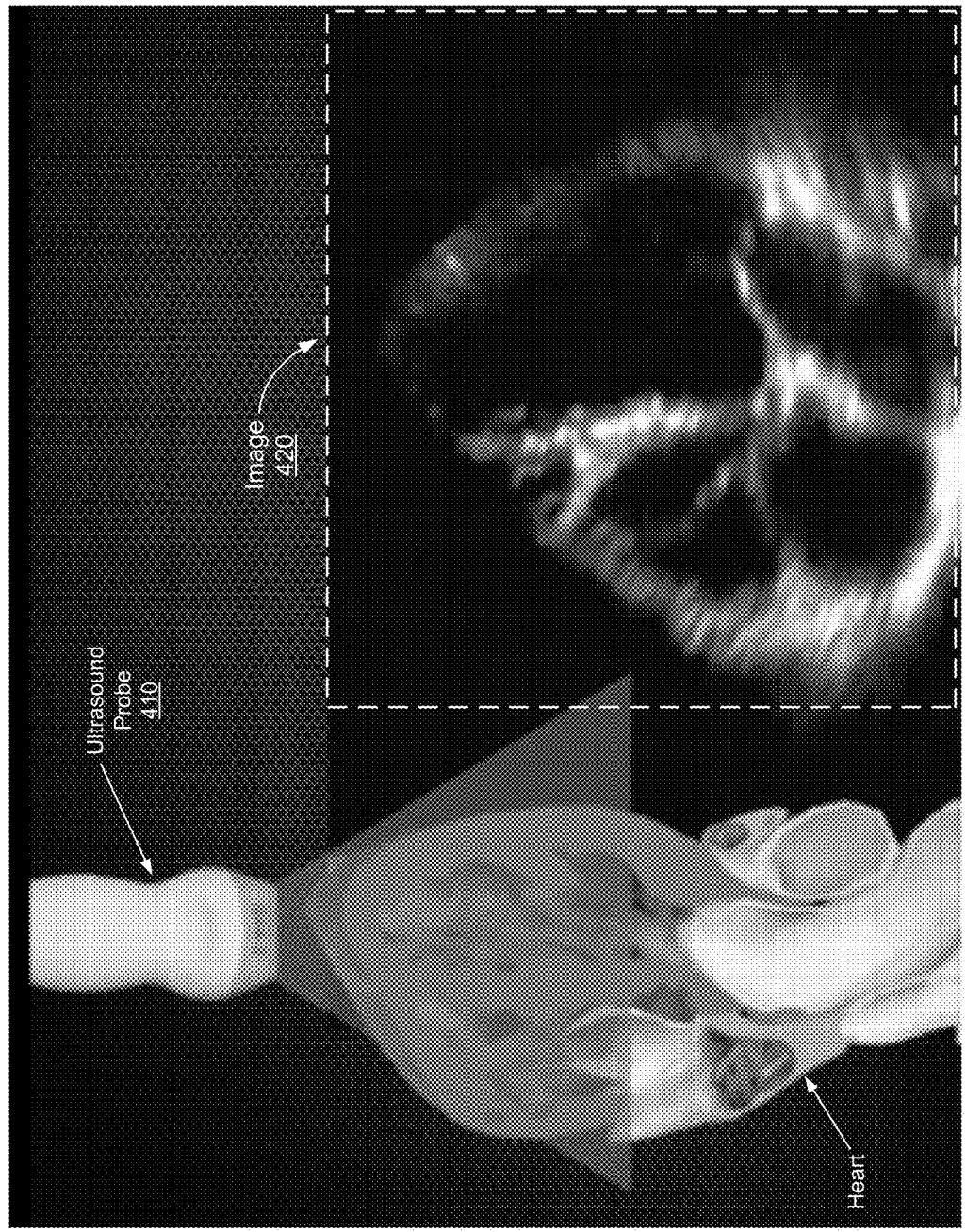
FIG. 4 illustrates an example use scenario when utilizing a medical imaging system during heart examination.

FIG. 4 illustrates an example use scenario when utilizing a medical imaging system during heart examination. Shown in FIG. 4 is an ultrasound probe 410 of an example ultrasound system (e.g., the ultrasound system 200 of FIG. 2) being used in imaging a patient's heart, which results in generation of corresponding ultrasound image(s) 420.

In this regard, medical imaging systems (e.g., ultrasound imaging systems) may be used in examining patients' hearts, such as to determine and/or assess whether (or not) the hearts are functioning properly. In such use scenarios, various parameters/indicators related to the heart and/or function(s) thereof may be measured, determined, and/or assessed during and/or based on imaging of the heart. One such indicator is ejection fraction (EF), which is the percentage of blood ejected from the left ventricle of the heart in a cardiac cycle (heartbeat).

The EF may be calculated based on other measurements/parameters associated with the heart and/or its functions—namely, the stoke volume (SV), the end diastolic volume (EDV) and the end systolic volume (ESV), with ejection fraction (EF) being calculated using the formula: EF=SV/EDV (multiplied by 100 to represent the EF as % value), and where the stroke volume (SV) is given by: SV=EDV−ESV. Ejection fraction (EF) is an important indicator for systolic function, with normal range being 50%-75%. As such, ejection fraction (EF) may be used as a measure of the pumping efficiency of the heart, and may be used for diagnostic purposes—e.g., being using to classify heart failure types. It is also used as an indicator of the severity of heart failure. Measurement and assessment of ejection fraction (EF) is very common in particular settings, such as in emergency room (ER) and intensive care unit (ICU) settings.

Various issues and/or challenges may arise with conventional approaches for performing imaging of heart, particularly with respect to measurement and/or assessment of parameters and/or indicators such as the ejection fraction (EF). For example, in conventional approaches, EF assessments may be done by manual tracing or eyeballing by expert. However, such approach may be time-consuming and unreliable. In this regard, there may be a need for performing such assessments faster and in more reliable manner. For example, there is a need for point of care ultrasound users to trend certain measurements over time. In this regard, it would be very useful to an emergency room (ER), intensive care unit (ICU) or anesthesia physician to see these measurements trending or averaging over multiple heartbeats.

In accordance with the present disclosure, medical imaging systems (such as the ultrasound system described with respect to FIG. 4) may be configured for providing enhanced heart imaging operations, such as by supporting real-time and automatic measurement and analysis of ejection fraction (EF), and preferably doing so over multiple heartbeats.

In various example implementations, medical imaging systems may incorporate real-time ejection fraction (EF) tool which may be configured for making the EF assessment automatically and in real-time, making these measurements easier to acquire. The EF tool may be implemented via suitable components in the medical imaging systems. For example, in the ultrasound system 200, the EF tool may be implemented via the signal processor 240, the heart imaging module 242, the training engine 270, etc.

In some implementations, the EF tool may be configured to analyze the heartbeats that are captured in the cine cache, while the EF tool is running—that is, while real-time automatic measurements of EF are being obtained. The EF tool may be configured to provide parameters obtained based on the EF measurement and/or analysis thereof, such as by displaying them via display (or other suitable visual output device(s)) of the medical imaging system. The parameters may be displayed, for example, in a graph with changes (e.g., over time, averages, and variance).

In an example implementation, the EF tool may be configured to operate based on images (or corresponding data) from Apical 4 Chamber (A4C) view.

In an example implementation, the EF tool may be configured to automatically identify particular structures in the heart (e.g., a particular ventricle, such as the left ventricle), such as based on processing of images captured or acquired during medical imaging of the heart. Identifying these structures may be pertinent for measuring and/or assessing various parameters or indicators associate with heart functions. In this regard, the automatic identifying of the particular structures in the heart may be performed using artificial intelligence and/or machine learning techniques, such as using deep learning techniques and/or algorithms (e.g., by use of deep neural networks, as described above).

In an example implementation, the EF tool (or, broadly, the imaging system incorporating the EF tool) may incorporate or support user interactions to relating to use of the EF tool and/or operations thereof (e.g., EF related measurements or analysis). For example, the medical imaging system may support or facilitating receiving user input relating to control of the EF tool and its operations—e.g., for activating the EF tool, control the duration of its running (e.g., number of heartbeats for which EF measurements are obtained), indicate when to analyze the EF measurement, etc. The medical imaging system may also support or facilitating providing user feedback relating to the EF tool and its operations (as well as the imaging operations performed in conjunction with the user of EF tool). For example, feedback (e.g., visual, audible, etc.) may be provided to the user to optimize the medical imaging used in generating the images used by the EF tool. In an example implementation this may be done by showing an icon (or similar visual representation) of the patient with a body marker showing where to position the probe.

In an example use scenario, when the user activates the EF tool, the EF tool may capture or measure data such as the end diastolic volume (EDV), the end systolic volume (ESV), the heart rate (HR), the cardiac output (CO), the ejection fraction (EF), the stroke volume (SV), etc. In this regard, the EF and SV may be measured as described above. The cardiac output (CO) given by: CO=SV×HR. The EF tool may be configured for determining at least some of the required measurements based on processing of captured images. For example, the EF tool may be configured for calculating the heart rate (HR) based on processing of images acquired during the medical imaging of the heart, to enable track movement of the heart (or particular structures thereof) thus allowing for counting heart beats. In some instances, capturing and/or measuring such parameters and/or indicators may entail or require identifying particular structures in the heart, such as the left ventricle, and the EF tool may be configured to automatically identify such structures, as described above.

When the user stops the tools (e.g., pressing a "freeze" button), there are many heart cycles in the cine cache, which may allow obtaining EF measurement over multiple heartbeats. In an example implementation, an input element (e.g., pressing a "analyze" button) may be provided, such as physical element in the system or as virtual element on the screen, which the user may be activate to perform the analysis, resulting in visual representation showing trending of these values over the multiple beats that are in the cine cache. This may allow showing trending of the parameters, an average over multiple beats and variance. An example graph is shown and described with respect to FIG. 5.

The EF tool (and use thereof) as described herein may offer many advantages and/or improvements over conventional solutions, particularly due to the EF tool's ability to automatically obtain EF measurements (as well as measurements of other indicators/parameter) in real-time, and to display multiple cardiac measurements, and to trend these measurements over multiple heartbeats. For example, based on conventional solutions, existing systems may only be configured to measure one parameter/indicator, and/or may require the user to make a new measurement and store it as an image in order to create a new plot point on the trending graph. The EF tool described herein is configured to obtain and trend multiple parameters, and does not require the user to take multiple, separate measurements to create a trending graph. Also, systems implemented in accordance with conventional solutions, if any exist, may only be able to provide EF results in one heartbeat. The EF tool described herein obtains and allows the user to view the EF, as well as other parameters, averaged over several cycles. Such capability (to average and show EF and other measurements over multiple heartbeats) may be particularly advantageous for detecting certain conditions—e.g., if the patient has an arrhythmia.

In various implementations, one or more different algorithms may be used (e.g., via the system components/circuitry implementing the EF tool) in performing and/or supporting various tasks and/or functions associated with real-time and automatic measurement of ejection fraction determination, assessment, and/or analysis. For example, convolutional neural network (CNN) algorithm(s) may be used for volumes processing, such as to detect the endocardium border frame-by-frame. Use of convolutional neural network (CNN) algorithm(s) in conjunction with EF and volumes related processing is described in more detail below.

For ejection fraction (EF), heart rate (HR), and systolic diastolic frames Fourier based algorithm may be may be applied, for example, on one of the endocardium points. An example heart rate and EOS/EOD frames algorithm may be configured such that it receives as input frame-by-frame estimated septal basal point y coordinate and volume (e.g., for 2.5-6 sec). The algorithm may then find main harmonic from Fourier, and then filters signal, and may find extremum points from clean signal on every harmonic interval. In some instances, the algorithm may incorporate post-processing such as to remove duplicates and/or add missing key frames. Thus, the algorithm may enable refining extremum points using volume signal.

For quality indication/indicator, classification convolutional neural network (CNN) algorithm(s) may be used. An example quality indicator algorithm may be implemented as Binary classification CNN, which have similar architecture to the CNN as described above and below. Such algorithm may be configured to run fast, such that it may be applied to multiple frames (e.g., once every 6 frames). In an example implementation, the quality indication/indicator algorithm may be configured such that all annotated 4-chamber view (4CH) images may be considered as the positive class. Further, equal total number of examples from other views (air, lungs, Inferior vena cava (IVC), veins, and other cardiac views) may be considered negative. In an example implementation, the quality indication/indicator algorithm may be further configured to incorporate additional features, such as using variation of x coordinate of the septal basal point as an estimator for "probe movement," decreasing QI score if some of the coordinates fall outside of the scan region, decreasing QI score if the estimated LV interior is not much darker than the estimated LV endocardium and wall, estimating image quality in addition to the view correctness, inference time augmentation, etc.

In various implementations, the architecture of convolutional neural network used in conjunction with the algorithm used or applied in the course of ejection fraction (EF) related operations may be adaptively adjusted to optimize performance. In this regard, the structure of the CNN may be set or adjusted based on various performance consideration, such as size of network, size of data, and performance (e.g., accuracy). For example, the structure of the CNN used in EF related functionality may be optimized for small size, small data, and high performance.

In various implementations, the software architecture used in implementing the EF tool may be adaptively configured for optimizing EF related functions, including based on used algorithms and/or other existing functions (or tools). For example based on existing tools, software architecture may be configured to provide image to EF related algorithm(s), which may then perform EF related calculations. The system software may then plot graphical results (as described above). In some instances, EF related algorithm(s) may receive only real display frames—that is, no interpolated frames. In various instances, rerunning of the tool may provide the exact same frames to the algorithm(s).

Figure 5:
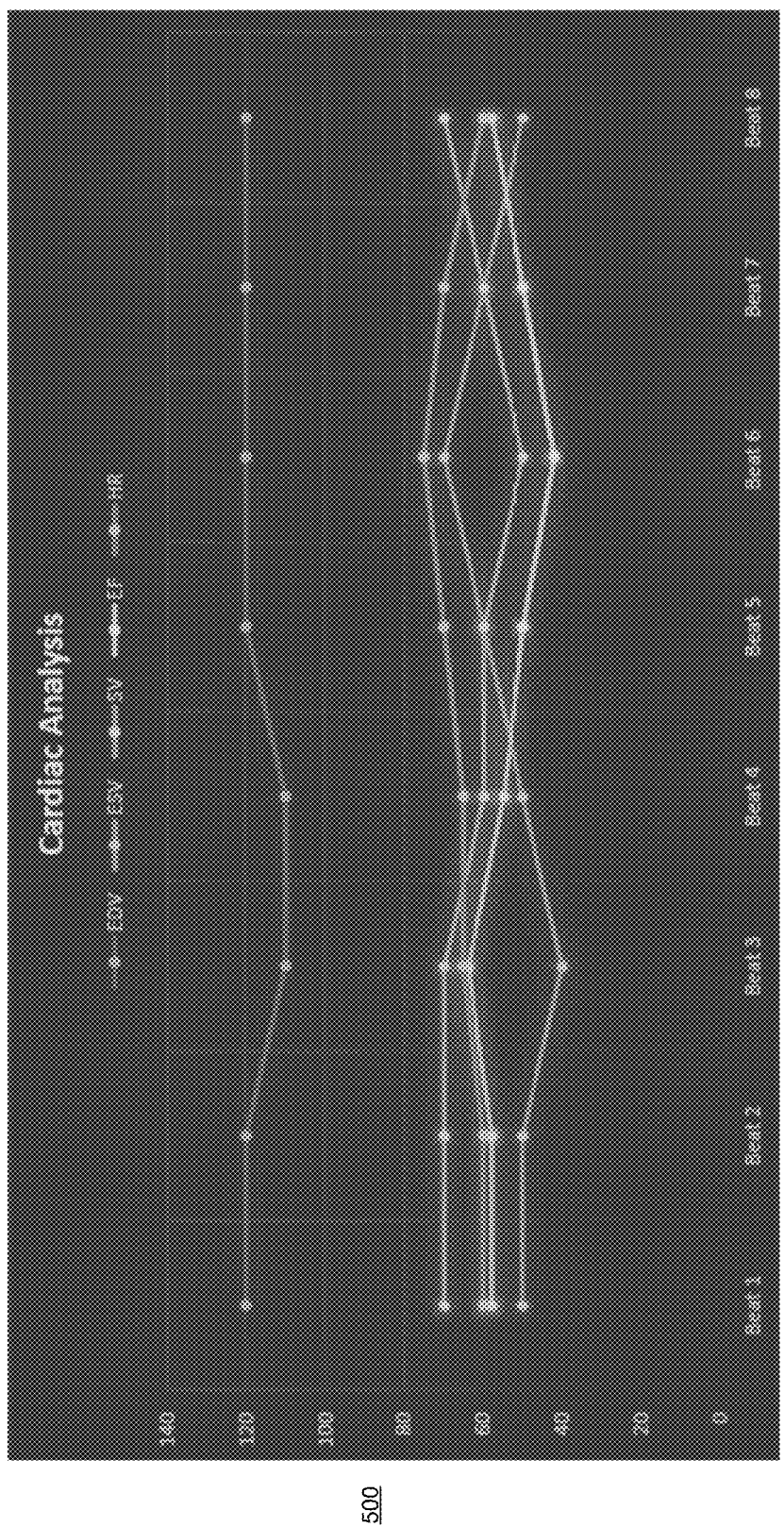
FIG. 5 illustrates a screenshot of an example graph generated based real-time and automatic ejection fraction (EF) analysis, in accordance with the present disclosure.

FIG. 5 illustrates a screenshot of an example graph generated based real-time and automatic ejection fraction (EF) analysis, in accordance with the present disclosure. Shown in FIG. 5 is a screenshot of a graph 500 displayed in a medical imaging system (e.g., the ultrasound system 200 of FIG. 2) configured for supporting real-time and automatic ejection fraction (EF) analysis, when providing results of real-time ejection fraction (EF) analysis.

The graph 500 may be generated in the medical imaging system via an ejection fraction (EF) tool similar to the tool described with respect to FIG. 4. For example, a user may activate the EF tool, the EF tool may capture or measure such parameters as end diastolic volume (EDV), end systolic volume (ESV), heart rate (HR), stroke volume (SV), and ejection fraction (EF). When the user stops the EF tool (e.g., pressing a "freeze" button) after 8 heartbeats, the parameters may be analyzed (including performing any necessary calculations, such as the EF values based on the other measurement), to generate corresponding results (as shown in the table below, illustrating results from an example 8-heartbeats run), and the graph 500 may be generated based on the results and provided via the display (or any suitable visual output component) of the medical imaging system.

TABLE 1 measurements for example 8-heartbeats run

|  | Beat 1 | Beat 2 | Beat 3 | Beat 4 | Beat 5 | Beat 6 | Beat 7 | Beat 8 | Average | Variance |
| --- | --- | --- | --- | --- | --- | --- | --- | --- | --- | --- |
| EDV | 120 | 120 | 110 | 110 | 120 | 120 | 120 | 120 | 117.5 | 18.75 |
| ESV | 50 | 50 | 40 | 50 | 60 | 70 | 60 | 50 | 53.75 | 73.44 |
| SV | 70 | 70 | 70 | 60 | 60 | 50 | 60 | 70 | 63.75 | 48.44 |
| EF | 58 | 58 | 64 | 55 | 50 | 42 | 50 | 58 | 54.4 | 40.48 |
| HR | 60 | 60 | 60 | 65 | 70 | 75 | 70 | 60 | 65.6 | 27.73 |

Figure 6A:
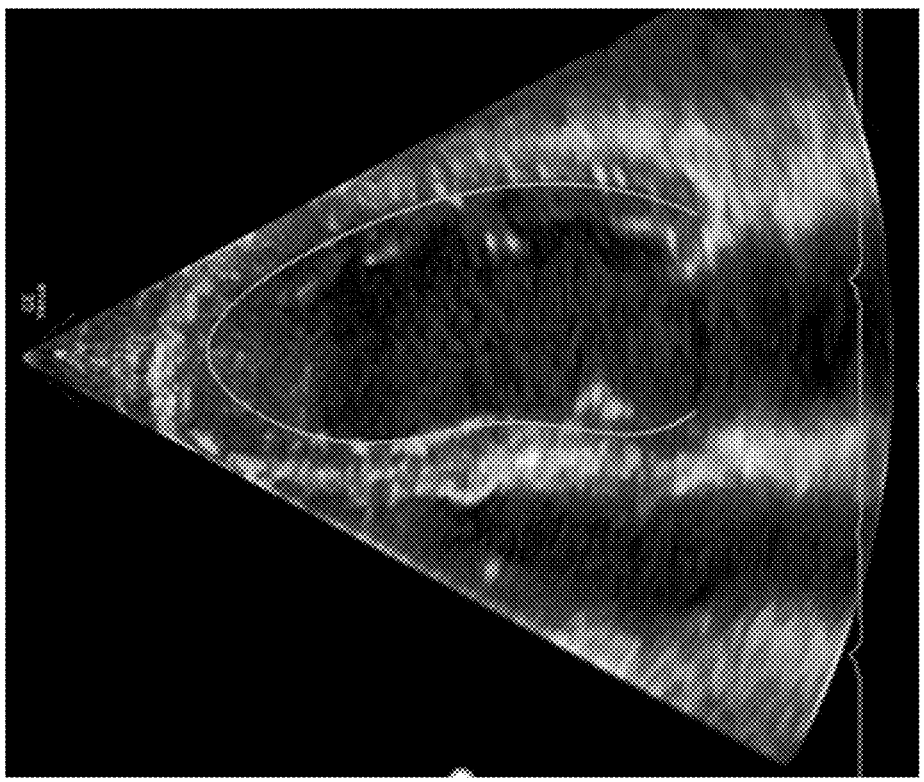
FIGS. 6A-6B illustrate an example workflow when performing real-time and automatic ejection fraction (EF) analysis in an example medical imaging system, in accordance with the present disclosure.
Figure 6B:
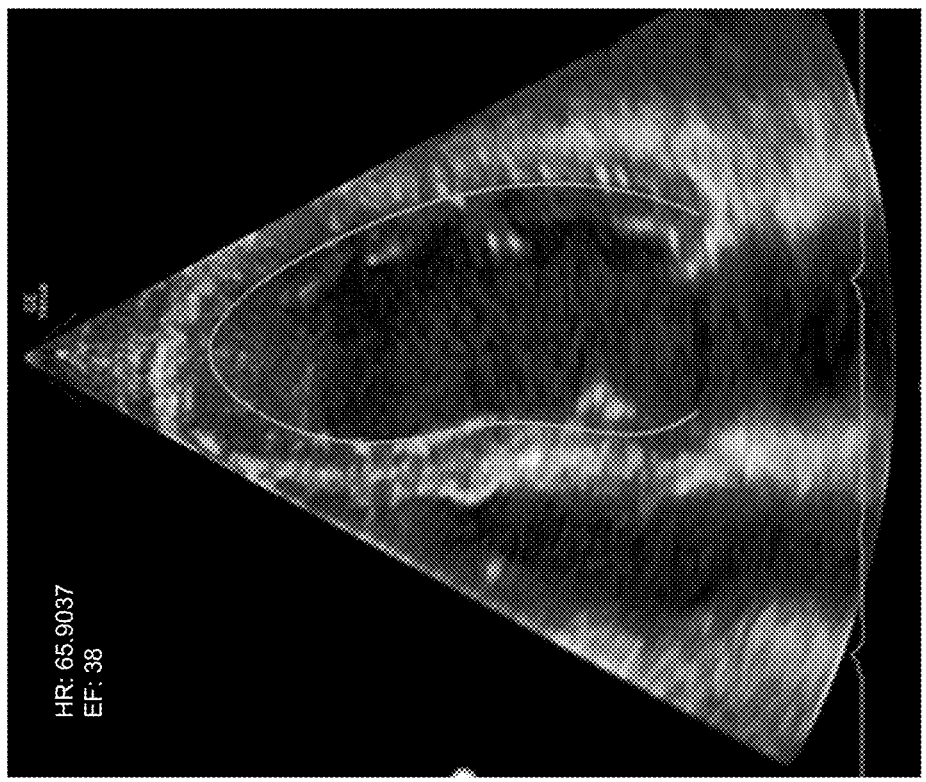

FIGS. 6A-6B illustrate an example workflow when performing real-time and automatic ejection fraction (EF) analysis in an example medical imaging system, in accordance with the present disclosure. In this regard, the workflow illustrated and described with respect to FIGS. 6A-6B may be executed via medical imaging system (e.g., the ultrasound system 200 of FIG. 2) that is configured for performing real-time and automatic ejection fraction (EF) analysis, such as using an ejection fraction (EF) tool similar to the tool described with respect to FIG. 4.

Shown in FIGS. 6A-6B is a live ultrasound image 600 (i.e., with elapsed time), which may be generated via the medical imaging system in the course of heart examination. The workflow may be initiated by activating the EF tool. At this point, endocardium enhancement may be displayed live on the ultrasound image. This may entail, for example, automatically identifying particular structures in the heart (e.g., the left ventricle), then segmenting the endocardial or ventricle wall of heart (e.g., by identifying the contour of the ventricle, then selecting particular points on the contour), then tracking the wall motion over time (e.g., based on tracking of the contour point(s)).

In some instances, the displaying of contour may be adaptively controlled, such as based on quality indicators which may indicate, for example, the confidence of the contour. For example, contour color (e.g., green for good, red for bad, yellow for intermediate, etc.) may be based on the quality indicator as determined based on the image. In some instances, the quality indicator may be shown with higher resolution and/or more gradations than were available during real time. For example, quality indicator may be binary in real-time and then have 3 or more gradations after scanning).

The EF tool may then automatically determine and/or calculate measurements relating to the EF analysis (e.g., EF, HR, etc.). The measurements may then be displayed, as shown in FIG. 6B. In this regard, because obtaining the measurements and/or performing the analysis may take some time from start (activation) of the tool, the displaying of measurement may be done after some delay (e.g., 2.5 sec).

Figure 7:
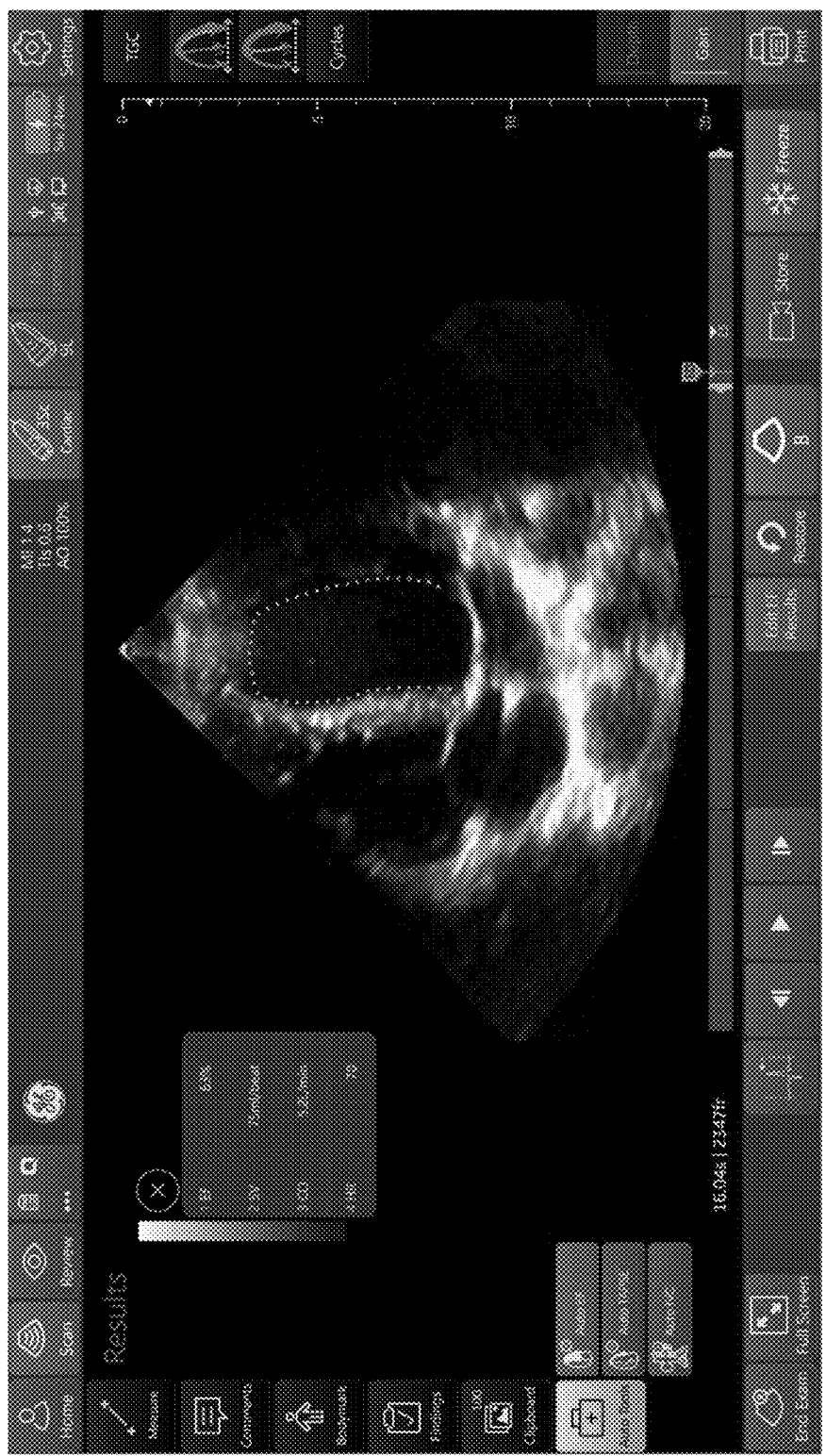
FIG. 7 illustrates a screenshot of an example graphical user interface (GUI) that may be used in conjunction with real-time and automatic ejection fraction (EF) analysis during medical imaging, in accordance with the present disclosure.

FIG. 7 illustrates a screenshot of an example graphical user interface (GUI) that may be used in conjunction with real-time and automatic ejection fraction (EF) analysis during medical imaging, in accordance with the present disclosure. Shown in FIG. 7 is a screenshot of a graphical user interface (GUI) 700 with support for real-time and automatic ejection fraction (EF) analysis.

The GUI 700 may be implemented in a suitable medical imaging system (e.g., the ultrasound system 200 of FIG. 2) that configured for supporting real-time and automatic ejection fraction (EF) analysis, when providing results of real-time ejection fraction (EF) analysis, with the GUI 700 being presented via suitable output component (e.g., screen or other display component) of the system. For example, as shown in FIG. 7, the GUI 700 may incorporate EF tool related input elements, such as for activating the tool, freezing the live feed (e.g., after a number of heartbeats), analysis related selection buttons, etc. The GUI 700 may be used in the course of workflow of real-time and automatic ejection fraction (EF) analysis.

For example, with reference to the live image 600 described above, with EF and HR values displayed in the image, the user may utilize the GUI 700 to perform EF analysis. The image feed in the GUI 700 may jump to last good cycle EOS frame, with the EOS and EOD markers appearing on cine scroll bar. When analysis is requests, the result of automatic EF analysis may be displayed within the GUI 700 (as shown in FIG. 7).

In an example implementation, convolutional neural network (CNN) may be used during real-time and automatic ejection fraction (EF) analysis, such as during use of a medical imaging system in the course of heart examination support for real-time and automatic ejection fraction (EF) analysis. In this regard, medical images generated in the medical imaging system may be subjected to convolutional neural network (CNN) based processing during real-time and automatic ejection fraction (EF) measurement and/or analysis. In this regard, as noted above, convolutional neural network (CNN) algorithm(s) may be used within the AI framework implementing EF related functions, such as for EF and volumes related processing. The CNN algorithm may have a structure consisting of convolution, max pooling, dropout and fully connected layers. In example use scenario, the input may be a B-Mode A4C image (or portion thereof), and the output may be the contour. Further, Simpson's method of discs for measurement of echocardiographic end-diastolic and end-systolic left ventricular volumes.

Figure 8A:
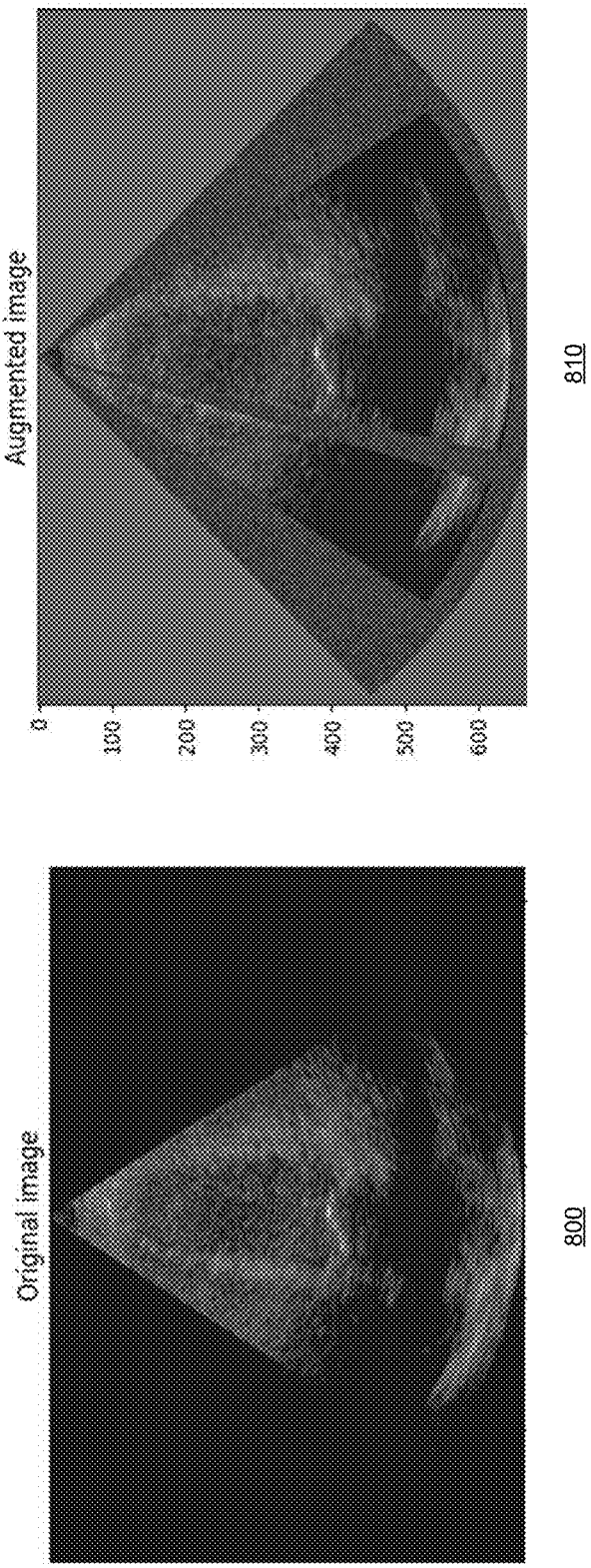
FIGS. 8A-8B illustrate an example use of augmentation of images in an example medical imaging system, in accordance with the present disclosure.
Figure 8B:
Figure 8B:

FIGS. 8A-8B illustrate an example use of augmentation of images in an example medical imaging system, in accordance with the present disclosure. Shown in FIGS. 8A-8B are snapshots of images generated in a medical imaging system (e.g., the ultrasound system 200 of FIG. 2) configured for supporting image augmentation.

Image augmentation may be utilized during training, such as to enhance quality of processing performed in the course of real-time and automatic ejection fraction (EF) measurement and/or analysis. For example, continuous augmentation may be done each time an image (e.g., image 800 of FIG. 8A) is selected for training. In this regard, the image may undergo a different random set of transformations, including, e.g., one or more of: rotation, translation, zoom, gain manipulations, changing depth, width, adding streaks of noise, and non-rigid transformations. This results in corresponding augmented image (e.g., image 810 of FIG. 8A). Further, in some instances, additional adjustments may be applied, such as by cropping depth as illustrated by images 820 and 830 of FIG. 8B.

An example system, in accordance with the present disclosure, comprises a medical imaging device comprising at least one processor, wherein the medical imaging device is configured to acquire one or more medical images during examination of a heart of a patient, and display the one or more medical images via a display device. Further, the processor is configured to, in real-time during the examination of the heart, process the one or more medical images; automatically identify at least one structure of the heart; automatically identify a contour of the at least one structure; indicate the contour in the one or more medical images, during the displaying of the one or more medical image; and provide during the indicating of the contour, a quality indicator associated with the contour. The at least one structure comprising a ventricle, a non-ventricle (e.g., epicardial wall), more than one ventricle (e.g., structure comprising all 4 ventricles of a fetal heart, etc.

In an example embodiment, the processor is further configured to measure or calculate during the examination of the heart, based on processing of the one or more medical images, one or more parameters and/or indicators associated with function of the heart during the examination of the heart.

In an example embodiment, the processor is further configured to provide during the examination of the heart, based on processing of the one or more medical images, feedback or output relating to one or more parameters and/or indicators associated with function of the heart during the examination of the heart.

In an example embodiment, the processor is further configured to automatically and in real-time calculate, based on processing of the one or more medical images, ejection fraction (EF) of the heart; and provide feedback relating to the calculated EF during the displaying of the one or more medical images.

In an example embodiment, the processor is further configured to utilize artificial intelligence in identifying the at least one structure and/or the contour of the at least one structure.

In an example embodiment, the processor is further configured to implement deep learning deep learning based neural networks for use in identifying the at least one structure and/or the contour of the at least one structure.

In an example embodiment, the processor is further configured to, when automatically identify a contour of the at least one structure, identify a plurality of contour points; and track trajectories of plurality of contour points during cycles over one or more complete heart beat cycles.

In an example embodiment, the processor is further configured to assess function of the heart based on tracking of the trajectories of plurality of contour points.

In an example embodiment, the processor is further configured to adaptively control the providing quality indicator associated with the contour based on a value or a classification of the quality indicator.

In an example embodiment, the processor is further configured to visually adjust a feedback or output corresponding to the quality indicator based on the value or the classification of the quality indicator.

An example non-transitory computer readable medium, in accordance with the present disclosure, may have stored thereon it a computer program having at least one code section, the at least one code section being executable by a machine comprising at least one processor, for causing the machine to perform one or more steps comprising acquiring one or more medical images during examination of a heart of a patient; displaying the one or more medical images; and in real-time, during the examination of the heart, processing the one or more medical images; automatically identifying at least one structure of the heart; automatically identifying a contour of the at least one structure; indicating the contour in the one or more medical images, during the displaying of the one or more medical image; and providing during the indicating of the contour, a quality indicator associated with the contour. The at least one structure comprising a ventricle, a non-ventricle (e.g., epicardial wall), more than one ventricle (e.g., structure comprising all 4 ventricles of a fetal heart, etc.

In an example embodiment, the one or more steps further comprise measuring or calculating during the examination of the heart, based on processing of the one or more medical images, one or more parameters and/or indicators associated with function of the heart during the examination of the heart.

In an example embodiment, the one or more steps further comprise providing during the examination of the heart, based on processing of the one or more medical images, feedback or output relating to one or more parameters and/or indicators associated with function of the heart during the examination of the heart.

In an example embodiment, the one or more steps further comprise automatically and in real-time calculate, based on processing of the one or more medical images, calculating ejection fraction (EF) of the heart; and providing feedback relating to the calculated EF during the displaying of the one or more medical images.

In an example embodiment, the one or more steps further comprise utilizing artificial intelligence in identifying the at least one structure and/or the contour of the at least one structure.

In an example embodiment, the one or more steps further comprise implementing deep learning deep learning based neural networks for use in identifying the at least one structure and/or the contour of the at least one structure.

In an example embodiment, the one or more steps further comprise, when automatically identify a contour of the at least one structure, identifying a plurality of contour points; and tracking trajectories of plurality of contour points during cycles over one or more complete heart beat cycles.

In an example embodiment, the one or more steps further comprise assessing function of the heart based on tracking of the trajectories of plurality of contour points.

In an example embodiment, the one or more steps further comprise adaptively controlling the providing quality indicator associated with the contour based on a value or a classification of the quality indicator.

In an example embodiment, the one or more steps further comprise visually adjusting a feedback or output corresponding to the quality indicator based on the value or the classification of the quality indicator.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a)

conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system comprising:
    a medical imaging device comprising at least one processor, wherein the medical imaging device is configured to:
        acquire a plurality of medical images during examination of a heart of a patient; and
        display the plurality of medical images via a display device; and
    wherein the processor is configured to:
        process the plurality of medical images;
        automatically identify at least one structure of the heart;
        automatically identify a contour of the at least one structure;
        utilize artificial intelligence (AI) in automatically identifying one or both of the at least one structure and the contour of the at least one structure, wherein the artificial intelligence (AI) is configured for one or both of analysis of heart functions and real-time automatic ejection fraction (EF) measurement or analysis;
        track the contour over two or more of the plurality of medical images;
        indicate the contour in the two or more of the plurality of medical images, during the displaying of the plurality of medical images; and
        provide during the indicating of the contour, one or more quality indicators associated with the contour, wherein at least one quality indicator is determined based on, at least in part, the tracking of the contour over the two or more of the plurality of medical images.

2. The system of claim 1, wherein the processor is configured to measure or calculate during the examination of the heart, based on processing of the plurality of medical images, one or more parameters and/or indicators associated with function of the heart during the examination of the heart.

3. The system of claim 1, wherein the processor is configured to provide during the examination of the heart, based on processing of the plurality of medical images, feedback or output relating to one or more parameters and/or indicators associated with function of the heart during the examination of the heart.

4. The system of claim 1, wherein the processor is configured to:
    automatically and in real-time calculate, based on processing of the plurality of medical images, ejection fraction (EF) of the heart; and
    provide feedback relating to the calculated EF during the displaying of the plurality of medical images.

5. The system of claim 1, wherein the processor is configured to implement deep learning deep learning based neural networks for use in identifying the at least one structure and/or the contour of the at least one structure.

6. The system of claim 1, wherein the processor is configured to, when automatically identify a contour of the at least one structure:
    identify a plurality of contour points; and
    track trajectories of plurality of contour points during cycles over one or more complete heart beat cycles.

7. The system of claim 6, wherein the processor is configured to assess function of the heart based on tracking of the trajectories of plurality of contour points.

8. The system of claim 1, wherein the processor is configured to adaptively control providing at least one quality indicator of the one or more quality indicators associated with the contour based on a value or a classification of the at least one quality indicator.

9. The system of claim 8, wherein the processor is configured to visually adjust a feedback or output corresponding to the at least one quality indicator based on the value or the classification of the at least one quality indicator.

10. A non-transitory computer readable medium having stored thereon, a computer program having at least one code section, the at least one code section being executable by a machine comprising at least one processor, for causing the machine to perform one or more steps comprising:
    acquiring a plurality of medical images during examination of a heart of a patient;
    processing the plurality of medical images;
    automatically identifying at least one structure of the heart;
    automatically identifying a contour of the at least one structure;
    utilizing artificial intelligence (AI) in automatically identifying one or both of the at least one structure and the contour of the at least one structure, wherein the artificial intelligence (AI) is configured for one or both of analysis of heart functions and real-time automatic ejection fraction (EF) measurement or analysis;
    tracking the contour over two or more of the plurality of medical images;
    displaying the plurality of medical images;
    indicating the contour in the two or more of the plurality of medical images, during the displaying of the plurality of medical images; and
    providing during the indicating of the contour, one or more quality indicators associated with the contour, wherein at least one quality indicator is determined based on, at least in part, the tracking of the contour over the two or more of the plurality of medical images.

11. The non-transitory computer readable medium of claim 10, wherein the one or more steps further comprise measuring or calculating during the examination of the heart, based on processing of the plurality of medical images, one or more parameters and/or indicators associated with function of the heart during the examination of the heart.

12. The non-transitory computer readable medium of claim 10, wherein the one or more steps further comprise providing during the examination of the heart, based on processing of the plurality of medical images, feedback or output relating to one or more parameters and/or indicators associated with function of the heart during the examination of the heart.

13. The non-transitory computer readable medium of claim 10, wherein the one or more steps further comprise:

automatically and in real-time calculate, based on processing of the plurality of medical images, calculating ejection fraction (EF) of the heart; and providing feedback relating to the calculated EF during the displaying of the plurality of medical images.

14. The non-transitory computer readable medium of claim 10, wherein the one or more steps further comprise implementing deep learning deep learning based neural networks for use in identifying the at least one structure and/or the contour of the at least one structure.

15. The non-transitory computer readable medium of claim 10, wherein the one or more steps further comprise, when automatically identify a contour of the at least one structure:

identifying a plurality of contour points; and tracking trajectories of plurality of contour points during cycles over one or more complete heart beat cycles.

16. The non-transitory computer readable medium of claim 15, wherein the one or more steps further comprise assessing function of the heart based on tracking of the trajectories of plurality of contour points.

17. The non-transitory computer readable medium of claim 10, wherein the one or more steps further comprise adaptively controlling providing at least one quality indicator of the one or more quality indicators associated with the contour based on a value or a classification of the at least one quality indicator.

18. The non-transitory computer readable medium of claim 17, wherein the one or more steps further comprise visually adjusting a feedback or output corresponding to the at least one quality indicator based on the value or the classification of the at least one quality indicator.

19. The system of claim 1, wherein the processor is configured to perform in real-time during the examination of the heart one or more of processing of the plurality of medical images, identifying of the at least one structure, identifying of the contour of the at least one structure, tracking of the contour, indicating of the contour, and providing of the one or more quality indicators.

20. The system of claim 1, wherein the processor is configured to track the contour over multiple complete heart beat cycles.

21. The non-transitory computer readable medium of claim 10, wherein the one or more steps further comprise performing in real-time during the examination of the heart one or more of the processing of the plurality of medical images, the identifying of the at least one structure, the identifying of the contour of the at least one structure, the tracking of the contour, the indicating of the contour, and the providing of the one or more quality indicators.

22. The non-transitory computer readable medium of claim 10, wherein the one or more steps further comprise tracking the contour over multiple complete heart beat cycles.

* * * * *